(12) United States Patent
Pham

(10) Patent No.: US 6,197,030 B1
(45) Date of Patent: *Mar. 6, 2001

(54) ELASTIC LOADED RETRACTABLE PIN DEVICE FOR CRANIAL BONE ATTACHMENT

(76) Inventor: Christopher J. Pham, 27666 Parkview Blvd., Apartment 912, Warren, MI (US) 48092

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/000,828

(22) Filed: Dec. 30, 1997

(51) Int. Cl.$^7$ .................................................. A61B 17/56
(52) U.S. Cl. .................................... 606/72; 24/265 B
(58) Field of Search .......................... 606/63, 72, 73–80, 606/60, 61, 62, 104; 623/16, 18, 21; 411/21, 24, 28; 224/164; 24/265 B, 265 WS

(56) References Cited

U.S. PATENT DOCUMENTS

| | | | | |
|---|---|---|---|---|
| 2,392,092 | * | 1/1946 | Konikoff | 24/265 |
| 2,672,861 | * | 3/1954 | Jonas et al. | 128/92 |
| 3,693,496 | | 9/1972 | Koide . | |
| 4,237,875 | * | 12/1980 | Ternanini | 128/92 |
| 4,326,321 | * | 4/1982 | Colognoru | 24/265 B |
| 4,516,569 | | 5/1985 | Evans et al. . | |
| 4,554,914 | | 11/1985 | Kapp et al. . | |
| 4,564,308 | * | 1/1986 | Ikegami et al. | 403/166 |
| 4,629,463 | | 12/1986 | Grundei et al. . | |
| 4,858,601 | | 8/1989 | Glisson . | |
| 4,858,603 | | 8/1989 | Clemow et al. . | |
| 4,938,768 | | 7/1990 | Wu . | |
| 5,207,712 | | 5/1993 | Cohen . | |
| 5,257,995 | | 11/1993 | Umber et al. . | |
| 5,380,338 | | 1/1995 | Christian . | |
| 5,501,685 | | 3/1996 | Spetzler . | |
| 5,669,912 | | 9/1997 | Spetzler . | |

OTHER PUBLICATIONS

Manuel Dujovny et al., "Aneurysm Clips: Magnetic Quantification and Magnetic Resonance Imaging Safety"; *J. Neurosurg*, vol. 87, Nov. 1997, pp. 788–794.

* cited by examiner

*Primary Examiner*—Michael Buiz
*Assistant Examiner*—Wen Ngo
(74) *Attorney, Agent, or Firm*—Brooks & Kushman P.C.

(57) ABSTRACT

Elastic-loaded, retractable shank surgical pins having a hollow shank adapted to receive an elastic-loaded retractable shank can be inserted into the bone flap or into the walls of the skull cavity from which the bone flap has been removed, the retractable shank compressed against the elastic loading, and the bone flap placed into position in the skull cavity. The retractable shanks are allowed to expand outwards into corresponding holes positioned in the skull or bone flap, securing the latter in place without the necessity of protruding wires or other conventional locating devices. The pins need not be positioned parallel to each other, and may be spaced around the bone flap, preferably constituting the sole means of securing the bone flap in the skull cavity.

12 Claims, 4 Drawing Sheets

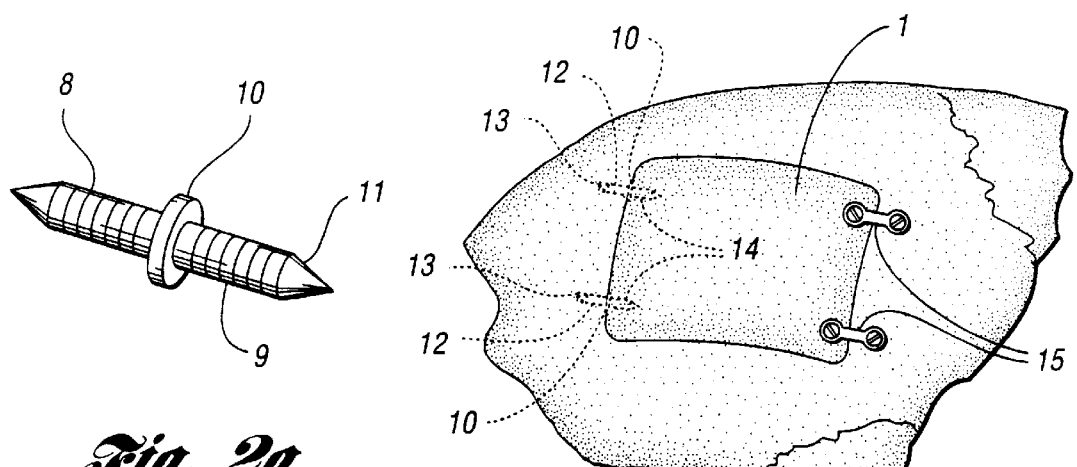
Fig. 2a (PRIOR ART)
Fig. 2b (PRIOR ART)
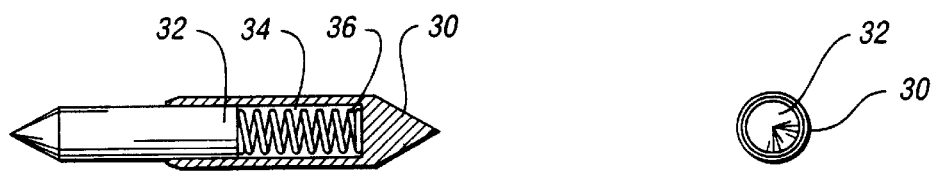
Fig. 3a
Fig. 3b
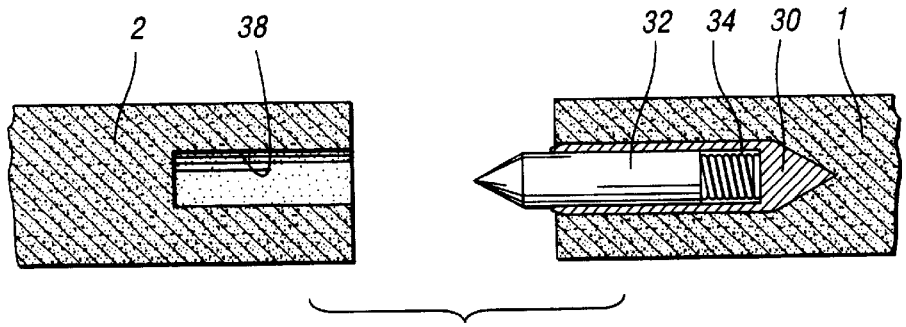
Fig. 3c
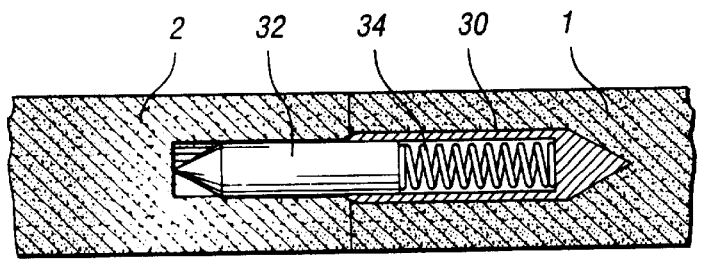
Fig. 3d

ELASTIC LOADED RETRACTABLE PIN DEVICE FOR CRANIAL BONE ATTACHMENT

TECHNOLOGICAL FIELD

The present invention pertains to pin-type devices useful for securing bone flaps in position following their removal in craniotomy and other surgical techniques. More particularly, the present invention pertains to pin-type devices having a retractable shank portion which is elastically loaded such that the pin, upon compressing and positioning over a passage in the skull or bone flap adapted to receive a pin, regains a substantial part of its uncompressed length. The present invention also pertains to a surgical kit containing one or more of the subject pin-type devices, and a surgical procedure directed to the use thereof.

BACKGROUND OF THE INVENTION

In many surgical procedures involving the cranium, a section of the skull bone (cranium) must be removed to provide access to the brain or other underlying tissue. The section removed may be round, square, or other shape dictated by the nature of the operation, the equipment available, the training of the surgeon, and the like. Following the operation, the bone flap removed must be repositioned and maintained stably for a period of time sufficient to allow the bone to knit together In the past, two principle methods have been used to secure the bone flap, as illustrated by FIGS. 1a and 1b. In FIG. 1a, a series of holes are drilled adjacent to each other along the mating peripheries of the skull and the bone flap. Wires are inserted through these holes and twisted or tied together to anchor the skull and bone flap in close proximity. The use of such wires causes several problems which are well recognized The protruding wire is apt to cause irritation due to either or both the normal motion of the scalp over the wires, or the palpation of the scalp over the wires Moreover, the protrusion of the wires above the surface of the cranium causes an elevation of the scalp at these positions, which may become more noticeable as scar tissue caused by relative movement of wires and scalp builds over time. This problem is aesthetically displeasing when a portion of the bone flap removed is below the patients hairline, or for balding patients, virtually anywhere. An improvement over the use of wires to maintain a bone flap in position is the use of screw-type devices as illustrated by FIG. 1b. However, these screw-type devices share some of the irritational and in large part, the disfiguring disadvantages of the use of wires.

In U.S. Pat. No. 5,669,912 are disclosed metal pins having two tapering shanks extending from a central protruding collar. One shank is pressed into the bone flap while the other shank is inserted into a hole in the skull positioned to receive the shank. The collar limits the degree of insertion into the bone flap. The device of the '912 patent is illustrated in FIG. 2a, and an application of the device is illustrated in FIG. 2b.

As can be seen in FIG. 2b, the use of the pins of the '912 patent is partially helpful in alleviating irritation and disfigurement by eliminating a number of wires and/or screw-type devices. However, the pins must be positioned parallel to each other and located on the same side of the bone flap, or they will be unable to enter the holes in the skull drilled to receive them. Thus, while one side of the bone flap may be secured with such pins, the remaining sides must be fixed in position with traditional fastening devices such as wires or screw-type fasteners.

SUMMARY OF THE INVENTION

The present invention pertains to a retractable pin-type device which is elastically loaded such that the pin, in its retracted position, may be positioned for entry into a corresponding hole in the skull, following which the retraction pressure is released, causing the retracted shank of the pin to enter the hole in the skull. Due to the ability of the skull-extending portion of the shank to retract prior to entry into the skull, when a plurality of the present devices are used, they are not required to be positioned parallel to each other, but may be distributed around the periphery of the bone flap, thus not requiring any wires or screw-type fasteners. Without any protrusions, irritation and disfigurement are substantially eliminated.

BRIEF DESCRIPTION OF THE DRAWINGS

FIG. 2a illustrates a prior art pin-type device used to position a skull flap;

FIG. 2b illustrates a skull flap positioned through use of two of the devices of FIG. 2a and two screw-type fasteners;

FIG. 3a illustrates one embodiment of an elastically loaded, retractable shank pin according to the subject invention;

FIG. 3b illustrates an end view of the device of FIG. 3a, viewed from the retractable shank end;

FIG. 3c illustrates a bone flap containing a retracted device of FIG. 3a being positioned proximate a shank-receiving hole in the skull;

FIG. 3d illustrates a bone flap secured in position by extension of the retracted shank portion, as illustrated by FIG. 3c, into the skull bone;

FIG. 4a illustrates a bone flap positioned through use of three of the devices of FIG. 3a;

FIG. 4b illustrates a bone flap positioned through use of four of the devices of FIG. 3a;

DETAILED DESCRIPTION OF THE INVENTION

Figure 1A:
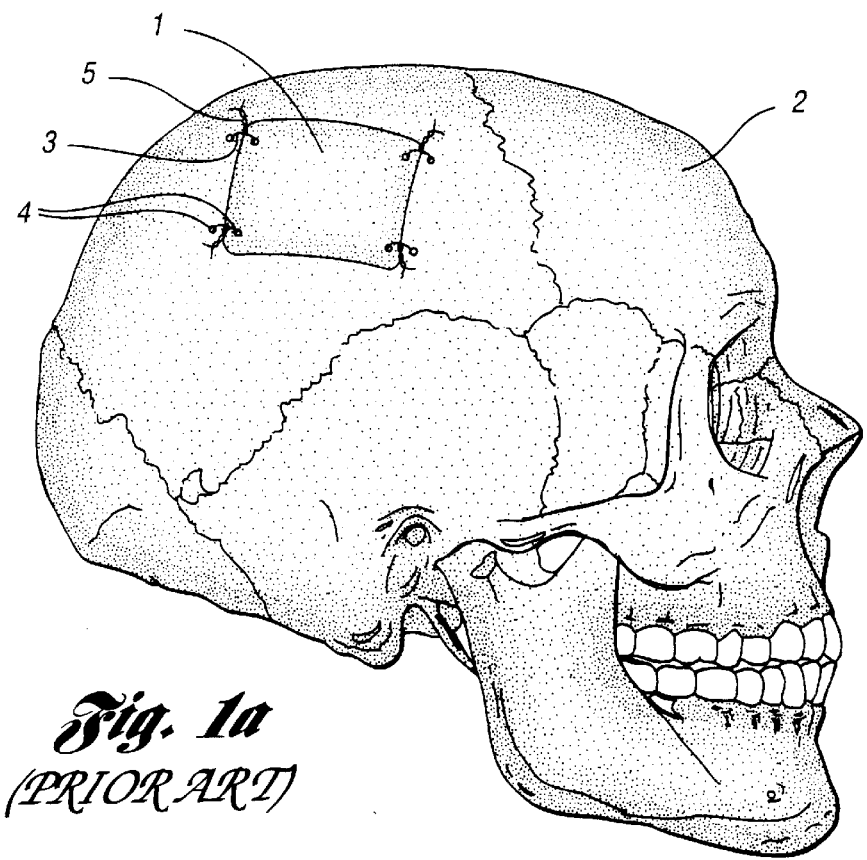
FIG. 1a illustrates prior art wire-type fasteners used to position a skull flap.
Figure 1B:
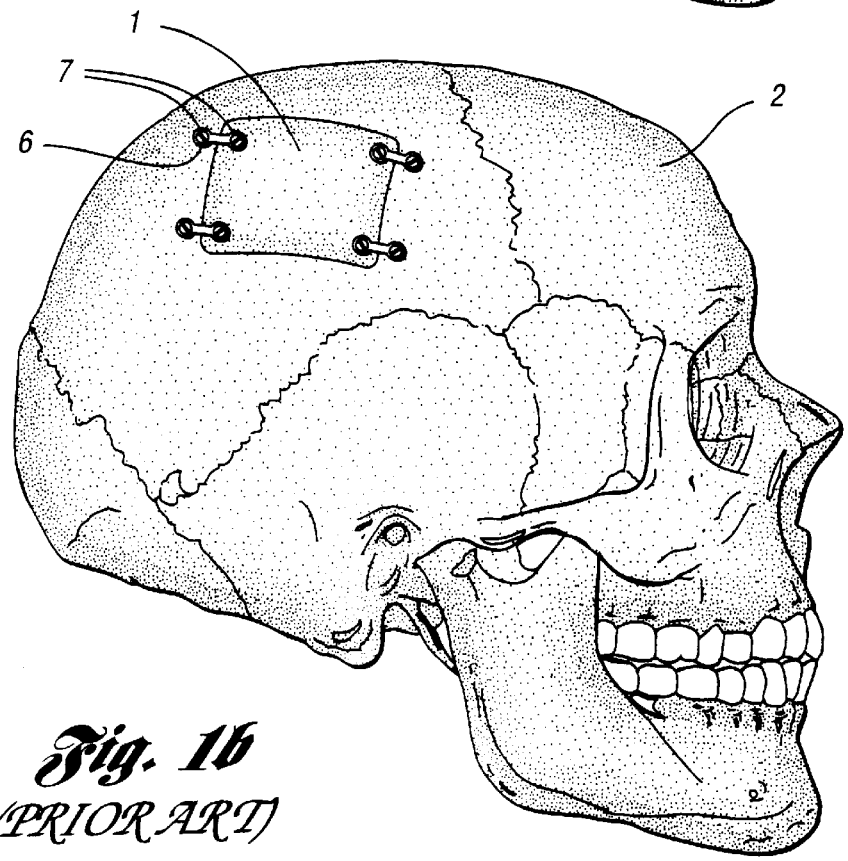
FIG. 1b illustrates prior art screw-type fasteners used to position a skull flap.

Prior art devices are illustrated by FIGS. 1a through 2b. In FIG. 1a, a bone flap 1 is maintained in position in the skull 2 by wires 3 which pass through holes 4 and are secured by twisting at 5. In FIG. 1b, screw-type fasteners consisting of a metal plate 6 bearing screws 7 are used to secure bone flap 1 in position in skull 2.

FIGS. 2a and 2b illustrate the pin devices of U.S. Pat. No. 5,669,912. In FIG. 2a, first shank 8 and second shank 9 extend from collar 10. Each shank tapers to a point 11. FIG. 2b illustrates the use of the prior art pins 2a in securing a bone flap. The skull shanks 12 are positioned parallel to each other on the same side of the bone flap in order that they may slide into parallel bores 13 in the skull. The collar 10 is located between the skull and the bone flap. In the bone flap, the bone flap shanks 14 are pressed into the bone. At the opposing side of the bone flap from the pins, screw-type devices 15 are used, as the pin-type devices of U.S. Pat. No. 5,669,912 cannot be used in these locations.

One embodiment of the subject invention, an elastic-loaded, retractable shank pin, is shown in FIG. 3a. In FIG. 3a, the pin comprises a first, hollow shank 30 and a second retractable shank 32 in nesting relationship with hollow shank 30. The second shank 32 is urged out of the receiving cavity 34 in hollow shank 30 by elastic member 36, in this case a coil spring. An end view of the device is shown in FIG. 3b. In FIG. 3c, the device is shown positioned in the bone of a bone flap 1 in retracted position, with spring 34 compressed. The bone flap and device are positioned to allow entry of the second, movable shank into a hole 38 drilled in the skull 2. On allowing the retractable shank 32 to be urged outward by spring 34, the respective shanks 32 and 30, positioned in bone flap 1 and skull 2, respectively, stably maintain an abutting relationship between the skull and bone flap as shown in FIG. 3d. Note that the absence of a collar allows close abutment of the skull and bone flap. Although the hollow shank portion is illustrated as positioned in the bone flap, reverse positioning is also possible, the hollow shank positioned in the skull bone.

Figure 4A:
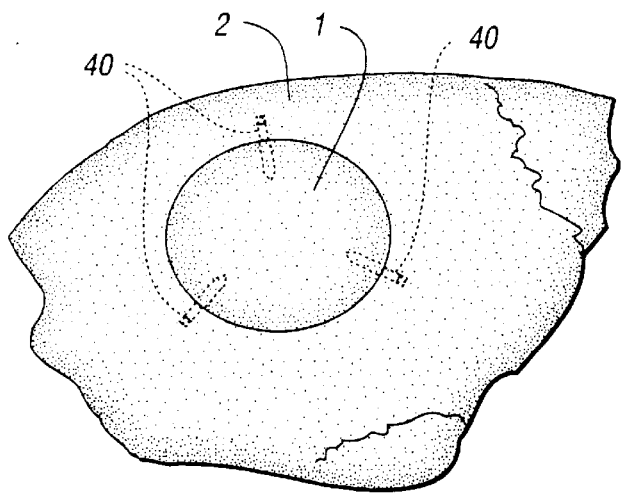
Figure 4B:
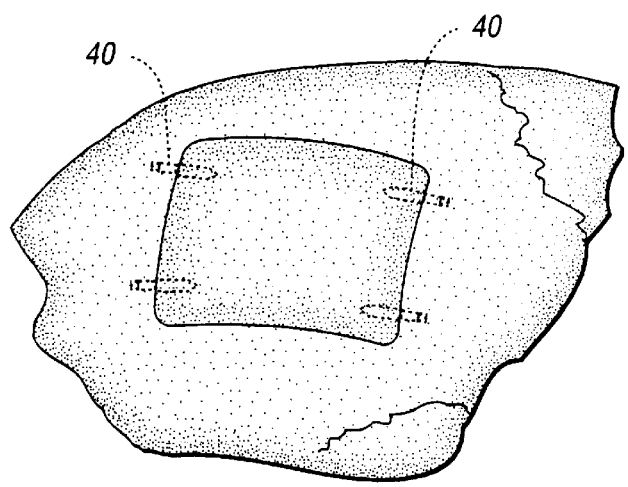

A view of skulls with bone flaps in place are shown in FIGS. 4a and 4b. In FIG. 4a, a circular bone flap having pins 40 radially distributed is shown, while in FIG. 4b, a rectangular flap is shown. Note that the pins do not have to be parallel, as shown in FIG. 4a, and that opposed pins may be used, as shown in FIG. 4b, which then does not require the use of wires, or screw-type fasteners as necessitated by prior art devices as illustrated in FIG. 2b.

Figure 5A:
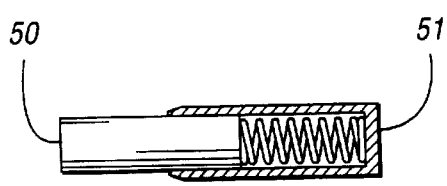
FIGS. 5a–5e illustrate alternative embodiments of the elastically loaded retractable shank pin devices of the subject invention.
Figure 5B:
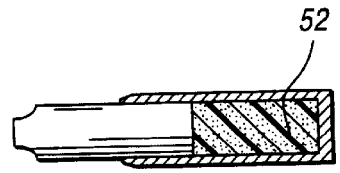
Figure 5C:
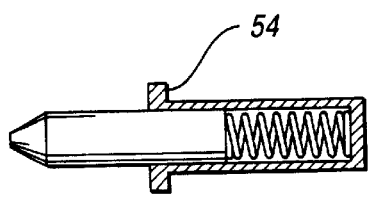

Alternative embodiments are shown in FIGS. 5a–5d. In FIG. 5a, a device with blunt ends 50 and 51 rather than pointed ends is shown. In FIG. 5b, a device having a compressible elastomer 52, e.g. a cellular or microcellular elastomer, rather than a spring elastic member is shown. In FIG. 5c, a device having an optional and less preferred flange 54 is shown.

Figure 5D:
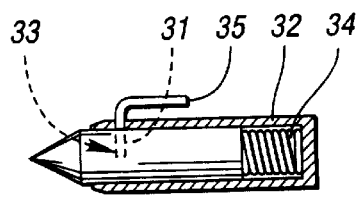
Figure 5E:
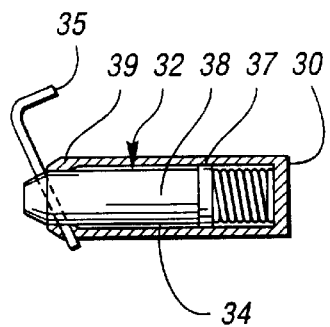

In FIG. 5d, a device having a retaining means in the hollow shank portion is shown. In FIG. 5d, the hollow shank portion 30 is bored to contain a small through passage 31. The shank 32 contains hole 33, which may also be a groove transverse to the axis of the shank. When compressed, the shank 32 is held in its retracted position by removable pin 35 as shown in FIG. 5e. Other retaining means are also suitable, for example a rotating, bayonet-type lock, with rotation provided by a movable pin operating in a slot in the hollow shank. Other retaining means equivalent to those described will suggest themselves to the skilled artisan.

In FIG. 5e is shown a further alternative embodiment of the subject elastic-loaded retractable shank pin devices. In FIG. 5e, the retractable shank 32 is machined with the innermost end 37 having a diameter substantially the same as the shank receiving cavity 34 of hollow shank portion 30. However, the remainder 38 of retractable shank 32 has a reduced diameter Following positioning of the retractable shank into the cavity 34, the lip 39 of hollow shank 30 are crimped along at least a portion of the lip circumference to a diameter less than the diameter of retractable shank portion 37, thus preventing retractable shank 32 from fully exiting the hollow shank by the outwardly urging force of the elastic loading member. In the device of 5e, the retraction retaining pin 35 is located in bores drilled at an angle into the retractable shank and hollow shank portion proximate the retractable shank receiving end of the hollow shank. This placement allows the hollow shank portion to be set more deeply into the receiving bone.

The elastic-loaded, retractable shank devices of the present invention are sized according to the needs of the patient and the location of the craniotomy, i.e. in particular, the thickness of the skull at the relevant areas. In general, the length of the device is from about 7 mm to about 1.5 cm, although shorter and longer devices can be employed where indicated. Diameter of the retractable shank may vary from about 0.3 mm to about 1.0 mm, while the hollow shank need be of sufficient diameter to receive the retractable shank while being of such wall thickness so as to provide the strength necessary to maintain the stability of the skull/bone flap interface. A diameter which is larger than the diameter of the retractable shank by from about 0.4 mm to about 1.0 mm is satisfactory, for example. The dimensions of the retractable shank and the hollow shank can be adjusted to higher or lower values depending upon the circumstances.

The elastic loading means is preferably a coil spring. However, compressible elastomers, particularly highly compressible, biocompatible elastomer foams may be used as well. When such foams are used, it is highly desirable to use a foam with high elastic recovery, i.e. low compression set. Silicone and polyurethane foams may be used, for example The material of which the elastic-loaded, retractable shank devices are constructed can be of any material with sufficient tensile strength, compressive strength, and modulus to maintain a stable skull/bone flap position. Materials of fully dense ceramic, reinforced thermoplastic or thermosetting engineer polymers, and metals may be used, for example. The various elements of the elastic-loaded, retractable pin devices need not be made of the same material. For example, a retractable shank may be constructed of fully dense ceramic while the hollow shank may be made of metal.

Preferably, the material of the elastic-loaded, retractable shank device is one which has a magnetic moment of less than 2 EMU/g, more preferably less than 1 EMG/g. Devices constructed of these materials, particularly those with magnetic moments of less than 1 EMU/g, are considered safe for use in magnetic resonance imaging (MRI). Examples of suitable metals having low magnetic moments are various austenitic stainless steels, for example nickel chromium stainless steels. Methods for testing materials to determine their suitability for MRI-sensitive applications and alloys suitable for such use are contained in the article "Aneurysm Clips: Magnetic Quantification And Magnetic Resonance Imaging Safety", Manuel Dujovny, M. D., et al., *J. NEUROSURG.* 87, pp. 788–794, 1977, incorporated for this purpose by reference.

Conventional craniotomy surgery techniques are used prior to insertion of the pins of the subject invention. Pin insertion can be accomplished by the methods disclosed in U.S. Pat. No. 5,669,912, which is herein incorporated by reference. In view of the variety of pin placements made available by the subject invention pins, the use of a boring guide is advisable in certain instances. A boring guide is a mechanical device which ensures that holes bored in the skull to receive the retractable pins are in proper location. The same device may be used to bore holes in the bone flap as well as the skull, assuring proper registration when pins are inserted.

Figure 6A:
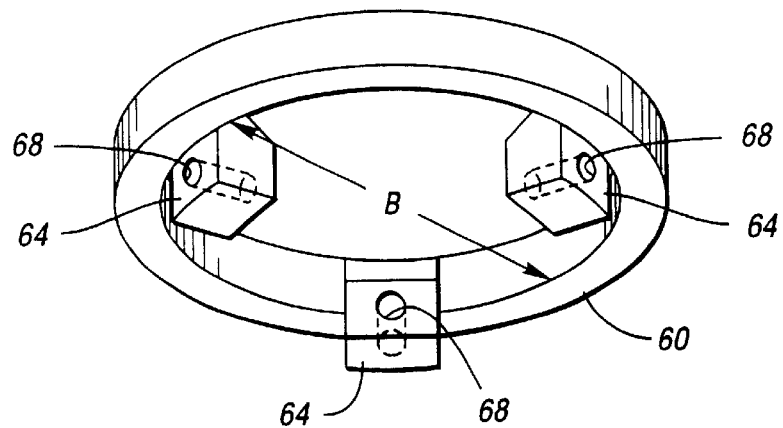
FIGS. 6a and 6b illustrate embodiments of boring guides suitable for use in craniotomy employing the subject invention pins.
Figure 6B:
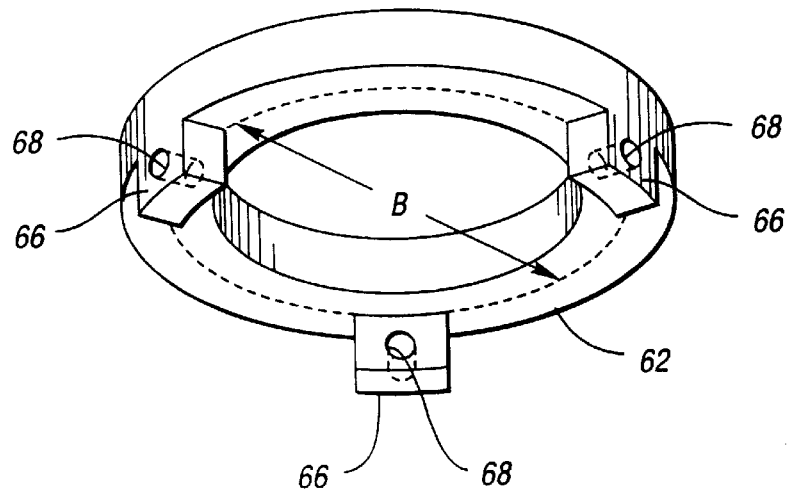

An example of a boring guide is illustrated in FIG. 6, and consists of two stainless steel rings 60 and 62 with guide blocks 64 and 66 extending below the ring. Guide blocks 64 are inset from the outer circumference of ring 60 and have drill guide bushings 68 through which the drill bit will pass from the inside of the guide block outwards to bore into the skull. The outer circumference of the ring is such that the plate will rest on the skull during drilling, while the inner diameter B is the diameter of the hole in the skull from which the bone flap has been removed. Boring guide ring 62 also has boring blocks 66 below it, but with the inner edges of the blocks lying along a circle with diameter B, i.e. a radius from the center of the boring guide of B/2. The inner circumference of the boring guide C is smaller than the bone flap outer diameter such that the device may rest atop the bone flap. The top of ring 62 may be left solid. The depth of the drill guide bushings 68 below the bottom of rings 60 and 62 is determined by desired pin placement depth and bone thickness. The height and spatial position of these blocks may also be made variable, for example by use of guide blocks located in rings 60 and 62 by means of a dovetail slot and corresponding extension. Upward and downward movement may be facilitated by similar guides located in two part guide blocks, or by the use of guide blocks of different heights. Square rings or rings of other shape, or alternative devices may be used as well. For example, the pins may be first pressed into place in the bone flap or located in holes drilled in the bone flap, and movable guide blocks adjusted to the proper positions, the pins retracted and the boring guide removed and placed on the skull to drill at the indicated positions.

The dimensions A and B may be standardized, and supplied in kit form with the necessary number of pins, or individual devices may be constructed from a clay, wax or other replica of the particular part of the cranium and a suitable boring guide prepared by stereo-lithography, lost wax, or other casting techniques. The boring guide may be made of robust thermoset or thermoplastic material or metal, the former preferably with metal drill bushing inserts.

By the term "substantially enter" as used herein is meant that the retractable shank shall be capable of retraction into the hollow shank such that any remaining protrusion of the retractable shank outside the hollow shank will yet allow for correct positioning of the bone flap within the skull cavity without exertion of undue pressure. Preferably, this protrusion will be no more than 1.5 mm, more preferably no more than 1 mm, and most preferably less than 0.7 mm. By the term "positioned congruent" as used herein is meant that drill guide positions are established which allow a retracted pin of an elastic-loaded, retractable pin device located in the corresponding mating bone of the bone surfaces to be located at a position to allow entry into the retracted pin receiving cavity Having now Lully described the invention, it will be apparent to one of ordinary skill in the art that many changes and modifications can be made thereto without departing from the spirit or scope of the invention as set forth herein.

What is claimed is:

1. A bone flap elastic-loaded, retractable shank pin device having a length between about 7 mm and about 1.5 cm and an outside diameter between about 0.3 mm to 1 mm suitable for positioning a bone flap in its respective cavity following crainiotomy, said pin comprising:

a) a retractable shank portion;
    b) a hollow shank adapted to slidingly receive said retractable shank portion;
    c) an elastic member contained in said hollow shank, said elastic member urging said retractable shank portion outwards from said hollow shank, and compressible to allow said retractable shank to substantially enter said hollow shank upon compression against said elastic member.

2. The elastic-loaded, retractable shank pin device of claim 1 wherein the material of construction of said device is one safe for use in MRI imaging.

3. The elastic-loaded, retractable shank pin device of claim 2 wherein at least one material of construction has a magnetic moment of less than 2 EMU/g.

4. The elastic-loaded, retractable shank pin device of claim 2 wherein at least one material of construction has a magnetic moment of less than 1 EMU/g.

5. The elastic-loaded, retractable shank pin device of claim 4 wherein said material comprises an austenitic stainless steel.

6. The elastic-loaded, retractable shank pin device of claim 1 wherein said elastic member comprises a coil spring.

7. The elastic-loaded, retractable shank pin device of claim 1 wherein said elastic member comprises a compressible elastomer.

8. An elastic-loaded, retractable shank pin device having a length between about 7 mm and about 1.5 cm and an outside diameter between about 0.3 mm to 1 mm, suitable for positioning a bone flap in its respective cavity following crainiotomy, said pin device comprising:

(a) a single retractable shank portion having a conical termination at its outermost end;
    (b) a hollow shank adapted to slidingly receive said retractable shank portion having a conical termination at its outermost end;
    (c) an elastic member contained in said hollow shank, said elastic member urging said retractable shank portion outwards from said hollow shank, and compressible to allow said retractable shank to substantially enter said hollow shank upon compression against said elastic member.

9. The retractable shank pin device of claim 8, wherein the retractable shank portion has a length which is a substantial fraction of the length of the hollow shank, and which when compressed, substantially enters the hollow shank.

10. The retractable shank pin device of claim 9, wherein not more than 1.5 mm of the retractable shank pin protrudes from the hollow shank when in a fully compressed condition.

11. The retractable shank pin device of claim 10, wherein not more than 1 mm of the retractable shank pin protrudes from the hollow shank when in a fully compressed condition.

12. The retractable shank pin device of claim 11, wherein not more than 0.7 mm of the retractable shank pin protrudes from the hollow shank when in a fully compressed condition.

* * * * *